US00PP13310P3

(12) United States Plant Patent
Sanders

(10) Patent No.: US PP13,310 P3
(45) Date of Patent: Dec. 3, 2002

(54) BEGONIA PLANT NAMED 'BEGOTIS'

(75) Inventor: Monica Sanders, Grootebroek (NL)

(73) Assignee: Syngenta Seeds B.V. (NL)

( * ) Notice: Subject to any disclaimer, the term of this patent is extended or adjusted under 35 U.S.C. 154(b) by 0 days.

(21) Appl. No.: 09/764,793

(22) Filed: Jan. 17, 2001

(65) Prior Publication Data

US 2002/0095706 P1 Jul. 18, 2002

(51) Int. Cl.[7] ..... A01H 5/00
(52) U.S. Cl. ..... Plt./343
(58) Field of Search ..... Plt./343

(56) References Cited

PUBLICATIONS

GTITM UPOVROM Citation for 'Begotis' as per NL PBR BGN0271; Oct. 21, 1999.*

* cited by examiner

*Primary Examiner*—Kent L. Bell
(74) *Attorney, Agent, or Firm*—Bruce Vrana

(57) ABSTRACT

A new Begonia plant particularly distinguished by its large, silvery white flower with intensive rose backside in outdoor plantings, giving a bicolor effect early flowering, an erect habit and easily self branching.

1 Drawing Sheet

BOTANICAL CLASSIFICATION

*Begonia obliqua×semperflorens.*

VARIETY DENOMINATION

'Begotis'.

BACKGROUND OF THE NEW PLANT

The present invention comprises a new and distinct cultivar of Begonia, botanically known as a cross between *begonia obliqua* and *Begonia semperflorens*. The new cultivar is propagated from cuttings resulting from the cross of P5106 and P 629. P5106 is a white flowering, green leaved *Begonia obliqua* and is not commercially available and is not known by any synonyms. *Begonia obliqua* is a medium leaved, shrub-like Begonia with single flowers and moderate flowering, mostly flowering in winter and spring. P 629 is a *Begonia semperflorens* and a plant from the commercial variety 'Milo red', an unpatented variety. P 629 is a semperflorens type Begonia, single flowered and profusely flowering. Neither P5106 or P 629 has been patented. As a result of this cross the present cultivar was created in 1996 in Enkhuizen, Netherlands and has been repeatedly asexually reproduced by cuttings in Enkhuizen, Netherlands over a four-year period. The instant cultivar has been found to retain its distinctive characteristics through successive propagations, and this novelty appears to be firmly fixed.

This new Begonia plant is an annual in most climatical zones in the U.S.

DESCRIPTION OF THE DRAWING

This Begonia plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new Begonia. The data that defines these characteristics were collected from plants which were asexually reproduced by cuttings, carried out in Enkhuizen, Netherlands. The plant history was taken on 1 year old plants, blossomed under natural light in a greenhouse. Color readings were taken in the office under natural daylight. Color references are primarily to The R.H.S. Color Chart of The Royal Horticultural Society of London.

THE PLANT

Classification — Botanical: *Begonia obliqua× semperflorens.*

Parentage:

*Female parent.*—A seedling named P5106 is one of our seedlings from our full sib-generation of plants bred in 1995.

*Pollen parent.*—A seedling named P 629 is one of our seedlings from 'Milo red'.

Growth habit: Erect, later spreading.
Plant height: Up to 80 cm.
Spreading area of plant: Up to 1 m.
Growth rate: Vigorous, easily self branching.
Strength: Good.
Branching character: Good branching.
Blooming period: Continuously, 4 weeks after potting the cuttings.

THE STEM

Diameter: 3–6 mm.
Shape: Round.
Anthocyanin pigmentation: Present, RHS 178A.
Length of internode: 20–80 mm, depending on the light where the plant is propagated.
Pubescence: No pubescence on the stem.
Length of stem: At end of season maximum 80 cm.

THE FOLIAGE

Phyllotaxis: Alternate.
Shape of blade: Ovate.
Base: Obtuse.
Apex: Acuminate.
Texture: Smooth.
Edge: Dentate.
Venation: Pinnate.
Length: 60–85 mm.
Width: 25–37 mm.
Color:
*Upper side.*—Deep green RHS 135A.
*Lower side.*—Brown red RHS 187A.
Pubescence: Some pubescence is present.
Petiole diameter: 2 mm.
Petiole color: Red (RHS 179B) when petiole is on the outside of the plant and receives a lot of light, otherwise green (RHS N144D).
Length of petiole: 8–22 mm.
Stipule: 2 per leaf.
Shape of stipule: Oblong.
Length of stipule: 10–14 mm.
Diameter of stipule: 4–7 mm.
Coloration of stipule: Green, RHS 144B with stripe of red RHS 179A.

THE BUD

Peduncle length: 58–63 mm, depending on season.
Peduncle diameter: 2 mm.
Peduncle color: RHS 179A.
Pedicel length: 21–24 mm.
Pedicel diameter: 1–2 mm.
Pedicel color: RHS 179B.
Bud size of male flower:
*Width.*—12–17 mm.
*Length.*—18–22 mm.
Shape: Ovate.
Color: Nearly white RHS 150D.
Sepals: No sepals.

THE FLOWER

Direction: Hanging.
Outward curvation of petal: Flat.
Male flower:
*Form.*—Cross shaped.
*Length.*—37–53 mm.
*Width.*—34–45 mm.
Female flower:
*Form.*—Star shaped.
*Width.*—24–38 mm.
Borne: Axillary.
Cluster: Cyme.
Cluster size: 10 cm.
Color of male large petal:
*Upper surface.*—White RHS 155C.
*Lower surface.*—Rose 63B.
Color of small male petal: White RHS N155C.
Color effect: Male flowers have rose backside of the large petals, and upper side of the large petals and the small petals is white. This gives a bicolor effect.
Color of female flower: White RHS N155B.
Texture of petals: Smooth.
Margin: Entire.
Overlapping of petals: Separate.
Number of petals: Male 4 and female 5.
Male flower — big petal: Oval, base is truncate, apex is obtuse.
Male flower — small petal: Oval, base is truncate, apex is obtuse.
Size of the big petal:
*Length.*—18–29 mm.
*Width.*—14–18 mm.
Size of the small petal:
*length.*—18–23 mm.
*Width.*—8–11 mm.
Number of stamens: 20.
Production of pollen: None observed.
Female flower: Oval, base is cuneate, apex is obtuse.
Size of the petal of the female:
*Length.*—16–18 mm.
*Width.*—7–9 mm.
Fragrance: No fragrance.
Number of flowers per cyme: 4–5 male flowers and 2–3 female flowers.
Reproductive organs: Male flowers have stamens, female flowers have a three-lobed stigma and receptacle under flower.
Lastingness of individual bloom: Ten days.
Number of flowers per plant: Maximum 400.
Seed production: No seed production observed.

ROOTS

Type of roots : Fibrous.
Physiological and ecological characteristics: Good tolerance to heat and cold. Strong resistance to pests and diseases.

What is claimed is:

1. A new and distinct variety of Begonia plant, substantially as herein illustrated and described.

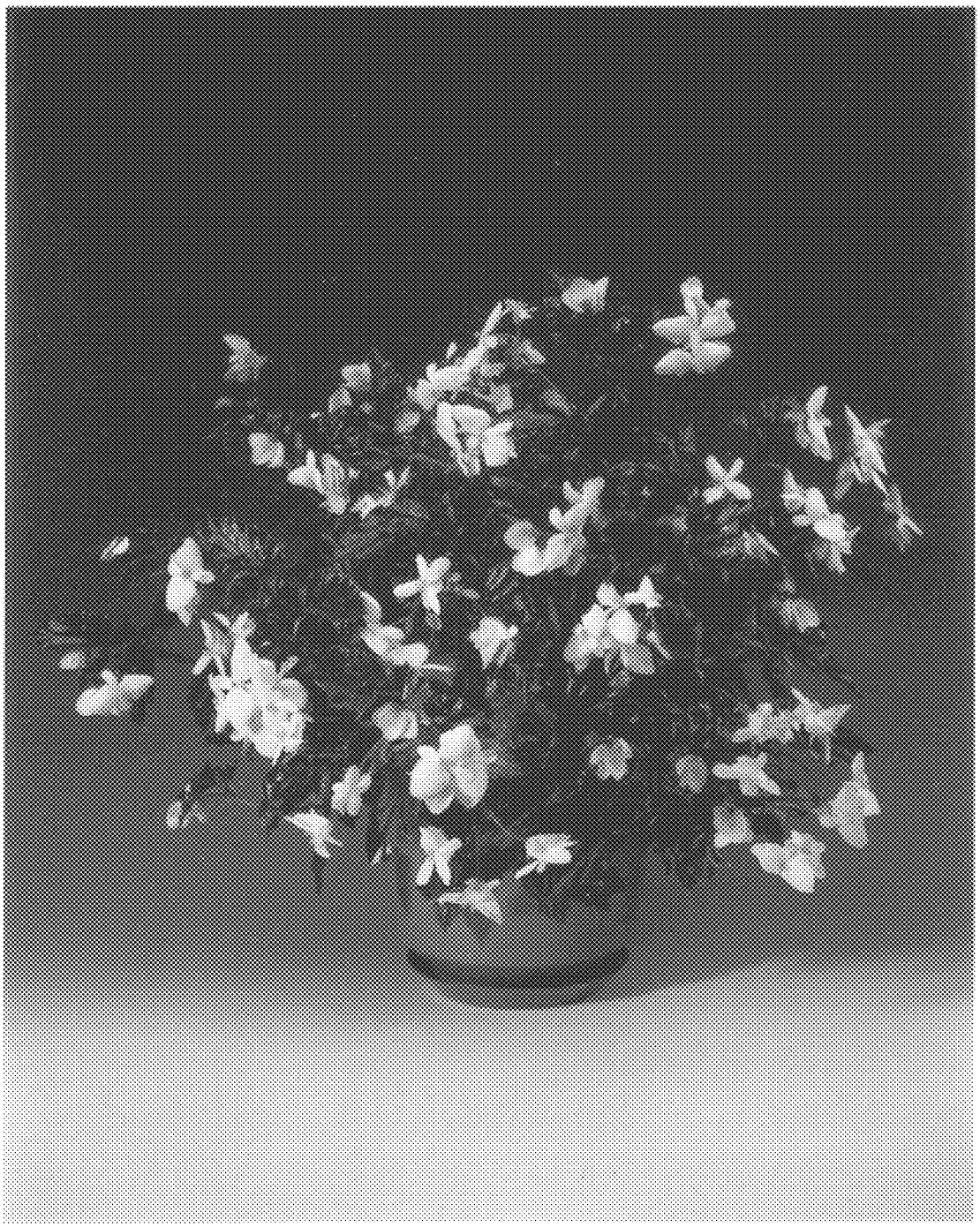

* * * * *